United States Patent [19]

Parsons, Jr. et al.

[11] 4,244,939
[45] Jan. 13, 1981

[54] BARBITURIC ACID TRACERS AND THEIR PREPARATION

[75] Inventors: George H. Parsons, Jr., Arlington; Ernest V. Groman, Somerville, both of Mass.

[73] Assignee: Baxter Travenol Laboratories, Inc., Deerfield, Ill.

[21] Appl. No.: 914,458

[22] Filed: Jun. 12, 1978

[51] Int. Cl.² ............... G01N 33/16; A61K 43/00
[52] U.S. Cl. .................... 424/1; 23/230 B; 260/112 B; 424/12; 544/299; 544/300; 544/301; 544/303; 544/305; 544/307
[58] Field of Search ............... 544/299–307; 424/1, 12; 23/230 B; 260/112 B

[56] References Cited

U.S. PATENT DOCUMENTS

| | | | |
|---|---|---|---|
| 3,817,837 | 6/1974 | Rubenstein et al. | 195/103.5 R |
| 3,995,021 | 11/1976 | Gross | 424/1.5 |
| 4,036,823 | 7/1977 | Soares | 424/1 |

Primary Examiner—Benjamin R. Padgett
Assistant Examiner—Christine M. Nucker

Attorney, Agent, or Firm—Paul C. Flattery; Lawrence W. Flynn; Max D. Hensley

[57] ABSTRACT

Compounds useful as tracers in the radioimmunoassay of barbiturates:

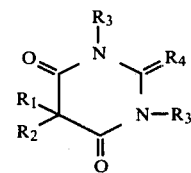

wherein
(a) $R_1$, $R_2$ and $R_4$ are identical to the substituents found at these positions in the barbiturate which is to be assayed;
(b) at least one $R_3$ is a radioiodinatable radical; and
(c) if only one $R_3$ is a radioiodinatable radical then the remaining $R_3$ is identical to the substituent found at this position in the barbiturate which is to be assayed; and the radioiodinated derivatives of said compounds.

31 Claims, No Drawings

BARBITURIC ACID TRACERS AND THEIR PREPARATION

This invention broadly relates to the radioimmunoassay of drugs related to barbituric acid. In particular, this invention relates to the radiolabeled barbiturate derivative employed in such assays, as well as the intermediates formed in making such derivatives and their methods of preparation of and use.

BACKGROUND OF THE INVENTION

Barbiturates are defined herein as pyrimidine derivatives in which the pyrimidine 2, 4 and 6 positions are occupied by carbonyl or thiocarbonyl radicals. Conventional radioimmunoassay methods for their determination generally employ a radiolabeled analogue of the barbiturate to be assayed, referred to hereinafter as a tracer. U.S. Pat. No. 3,766,162 discloses a barbiturate tracer in which the radioisotope $^{14}C$ is substituted for an nonradioactive barbiturate carbon atom. A more complex approach comprises modifying the barbiturate to provide a convenient site for radiolabeling the barbiturate. For example, U.S. Pat. No. 3,952,091 discloses that a pendant phenolic group capable of carrying $^{125}I$ may be introduced into secobarbital. The sole example given is 5-alkyl-5-[1-(p-hydroxyphenethyl-carbamyl)-2-propyl] barbituric acid which, it should be noted, is substituted with a radioiodinatable group at the 5 position of the barbiturate.

The use of such tracers in conventional radioimmunoassay procedures is well-known. For example, in the method commonly referred to as a competitive radioimmunoassay the tracer is allowed to compete with any test substance in the sample for a limited amount of antibody capable of binding both the tracer and the test substance. The antibody-bound tracer and test substance are then separated from the unbound material by conventional methods such as precipitation with a second antibody, antibody absorption on an insolubilized surface or the charcoal separation technique disclosed by Herbert et al., *J. Clin. Endocr.* 25, 1375–1384 (1965). The distribution of radioactivity between the two fractions is then determined. In the case of an assay for barbiturate, a surfeit of barbiturate in the test sample will result in a proportionately large number of antibody binding sites being occupied with nonradioactive barbiturate from the sample. On the other hand a sample largely devoid of barbiturate will ineffectively compete for the antibody binding sites, thereby resulting in proportionately high radioactivity in the bound phase. Other related radioimmunoassay methods which may be used with barbiturate tracers include the solid phase or double antibody separation techniques.

Tracers should exhibit certain characteristics for optimal use in radioimmunoassays. These include high specific tracer activity and high avidity of the antibody for the tracer and sample barbiturate. In the case of specific activity, each mole of tracer should emit as high a level of radioactivity as is commensurate with reagent stability and immunoreactivity. Thus, the higher the radioactivity emitted by the tracer the lower its detection limit becomes, and this in turn increases the sensitivity of the assay.

Antibodies should bind tracers with equally high avidity as the sample barbiturate to which the assay is directed. A large tracer substituent may inhibit binding of the tracer by antibody, particularly if the substituent is in the determinant region of the sample barbiturate. The consequence of this inhibition will be an assay indicating an erroneously high concentration of barbiturate.

Prior art barbiturate radioimmunoassays which employ radioiodinated moieties substituted at the 5 position of the pyrimidine ring are largely incapable of distinguishing among barbiturates or their metabolic products which differ from one another only at this position. This includes such barbiturates as barbital, phenobarbital, propallylonal and secobarbital as well as metabolites such as p-hydroxyphenobarbital. See, for example, "Clinical Chemistry," Vol. 23, No. 5, pages 873–876 (1977) in which it is reported that a barbiturate radioimmunoassay kit containing an $^{125}I$-labeled secobarbital derivative is subject to interference by p-hydroxyphenobarbital.

It is therefore a general object of this invention to provide new barbiturate derivatives which are useful in the preparation of tracers for the radioimmunoassay of barbiturates and which may be radioiodinated to provide the tracers themselves.

In particular, it is an object of this invention to obtain a barbiturate tracer which can be used in a radioimmunoassay capable of distinguishing among the various barbiturates of medical interest as well as their metabolites.

It is an additional object of this invention to prepare a tracer which will bind antibody with an avidity close to that of the barbiturate which is being assayed.

It is a further object of this invention to provide a tracer having high specific activity.

These and other objects of this invention will be apparent to those skilled in the art from a consideration of this specification taken in its entirety.

SUMMARY OF THE INVENTION

The above objectives are accomplished by using barbiturate tracers radiolabeled at the pyrimidine ring nitrogen atoms rather than at the ring 5 position. In particular, the above objectives are accomplished by novel barbiturate compounds having the formula:

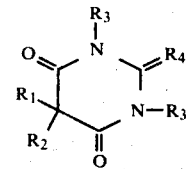

wherein
(a) $R_1$, $R_2$ and $R_4$ are identical to the substituents found at these positions in the barbiturate which is to be assayed;
(b) at least one $R_3$ is a radioiodinatable radical; and
(c) if only one $R_3$ is a radioiodinatable radical then the remaining $R_3$ is identical to the substituent found at this position in the barbiturate which is to be assayed; and including the radioiodinated derivatives of said compounds.

A radioiodinatable radical is defined as one which may be covalently substituted by at least one iodine atom without substituting or otherwise modifying any other portion of the barbiturate molecule. Radioiodinatable radicals which may be simultaneously substituted with another group or atom in addition to iodine, e.g., hydroxyl in the case of alkenes, are included within the scope of this definition. Those skilled in the art will readily recognize radicals which may be radioiodinated under mild conditions using known methods such as those disclosed herein. While straight or branched carbon chain alkanols or alkenes are radioiodinatable as defined above, most such radicals will contain radioiodinatable rings. These rings are ordinarily selected from the group of phenol, imidazole, indole, pyrrole, furan or thiophene rings. In order of preference are radioiodinatable rings, alkenes and alkanols.

The tracers of this invention are characterized by the presence of at least one radioiodinated radical at the 1 or 3, or 1 and 3 positions of the barbiturate ring. The radical may vary widely in structure as its purpose is to link the iodine radioisotope with the barbiturate moiety. If a tracer is substituted at both nitrogen atoms with such radicals, the radicals may be the same or different. Also, it is generally unimportant whether the tracer is mono-substituted at the 1 or the 3 positions.

Ordinarily the radioiodinated radical will be the group $L(Z)_n$ wherein L is a linking group, Z is a radioiodinated ring and n ranges from 1 to about 10. Since the linking group merely serves to bind the radioiodine-substituted ring Z to the barbiturate it may be selected from a wide variety of groups whose identity will be in part dependent upon the ease of synthesis. However, the linking group should not be so large as to sterically hinder antibody binding of tracer, nor should it contain substituents which would adversely react with the assay reagents or test samples. The total molecular weight of the $L(Z)_n$ moiety will not ordinarily exceed 2000 and is generally less than 1000. The linking group will also be polyfunctional where n is greater than 1, i.e., substituted with a plurality of radioiodinated rings. Generally only one such radical will be linked to the barbituric acid moiety. Representative linking groups are cyclic, normal or branched alkylenes or alkenylenes, such alkylenes and alkenylenes substituted with halo, hydroxy, keto, carboxy, alkoxycarbonyl, alkylamino or amino groups; ethers; carboxyl or phosphoryl esters; and amines or amides.

The ring-containing radicals are substituted or unsubstituted unsaturated rings. Generally the rings will also be heterocycles of nitrogen, oxygen or sulfur, or if not then hydroxyl-substituted carbocycles. Exemplary rings are substituted or unsubstituted phenol, imidazole, indole, pyrrole, furan or thiophene rings. A novel series of radioiodinatable compounds contain imidazole, pyrrole, furan or thiophene rings, with imidazole preferred.

Convenient processes for coupling the barbiturate radical to the radioiodinatable ring and simultaneously forming the linking group are disclosed in U.S. Pat. No. 4,036,823 or in copending U.S. application Ser. No. 673,853. For example, the barbiturate sodium salt may be reacted with the ω-halogenated lower alkyl ester of a desired carboxylic acid to produce the barbiturate-1,3-(ω-carboxylic acid ester). This ester is then converted to the corresponding acid by hydrolysis, which is then coupled to a suitable amino-substituted radioiodinated or radioiodinatable compound by carbodiimide condensation or by alkyl chloroformate activation of the carboxyl group. The amino-substituted derivatives are generally selected from the indole, phenol or imidazole aminoalkanes, aminoalkanols and alkanoic acids, for example, tyrosine, histidine, histamine, 4-hydroxyphenylglycine and tyrosinol. Amino-terminated polypeptide radicals containing at least one, usually two, of the aforesaid radioiodinatable rings may also be employed, although radicals containing more than about 10 of such rings are not preferred. The polypeptide as well as the tracer itself should be essentially incapable of raising antibodies upon injection into a suitable animal, i.e., neither should be antigenic or immunostimulative.

The tracers of this invention have broad use in any radioimmunoassay technique in which a sample is contacted with a constant amount of barbiturate tracer and an antibody which will selectively bind the sample barbiturate and barbiturate tracer, followed by measuring the degree of binding of the barbiturate tracer to the antibody. The tracer of this invention may be used with any of the various radioimmunoassays which employ a radiolabeled analogue of the substance tested, primarily including the competition and saturation methods.

DESCRIPTION OF THE PREFERRED EMBODIMENTS

The substituents $R_1$, $R_2$ and $R_4$, as well as $R_3$ when not representing a radioiodinated radical, are relevant only insofar as they represent the same substituents found in the barbiturate to which the assay is directed. A number of barbiturate drugs have been synthesized which differ at these positions. For the reasons discussed supra the barbiturate tracer should vary as little as possible from the sample barbiturate so as to successfully mimic its binding to the antibody. Thus, for example, a tracer useful in distinguishing phenobarbital from its p-hydroxyphenyl metabolite should have the structure of phenobarbital at its 5 positions. The structure of the relevant portions of the barbiturate to be assayed will be known at the time the barbiturate tracer is prepared, so it will be a simple matter to select the substituents at sites other than those to be occupied by radioiodinated radicals; the ordinary starting material for synthesis of the tracers will in fact be the barbiturate to which the assay is to be directed.

Representative substituents at the $R_1$ and $R_2$ positions are hydrogen, monohalosubstituted hydrocarbon, ether, thioether, or hydrocarbons including alkyl, alkenyl, cycloalkyl, cycloalkenyl or aryl of from 1 to about 8 carbon atoms. Exemplary hydrocarbons are phenyl, ethyl, n-butyl, n-hexyl, cyclohexen-1-yl, allyl and 1-methyl-2-pentenyl. $R_3$ is hydrogen or hydrocarbon of from about 1 to 4 carbon atoms. $R_4$ is oxygen or sulfur.

The following formulae represent exemplary barbiturates which may be assayed using tracers of this invention.

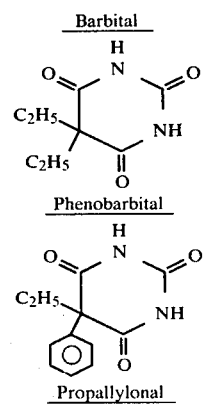

Barbital

Phenobarbital

Propallylonal

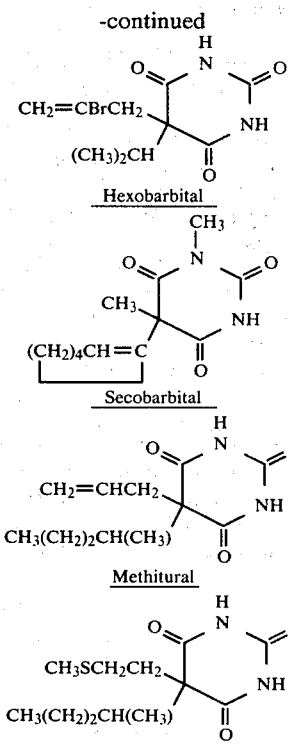

Hexobarbital

Secobarbital

Methitural

Other barbiturates include amobarbital, pentobarbital, butabarbital and thiopental.

The choice of salt or acid form of the barbiturate is not critical. However, it is preferred to use the alkali metal, e.g., sodium, salt of the barbituric acid derivative, both as a starting material in tracer synthesis as well as in the tracer itself.

Where a linking group is employed it could be selected from the following series:

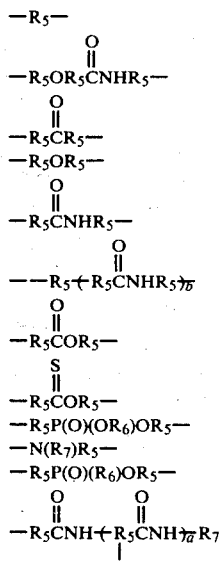

wherein $R_5$ is a bond; a substituted or unsubstituted hydrocarbon, ordinarily cyclic, normal or branched alkylene or alkenylene; or such alkylenes and alkenylenes substituted with halo, hydroxy, keto, carboxy, alkoxycarbonyl, amino or alkylamino groups; $R_6$ is alkyl of from 1 to about 6 carbon atoms; a ranges from 1 to about 10; b is 2 or 3; and $R_7$ is hydrogen; a substituted or unsubstituted hydrocarbon, ordinarily a normal, cyclic or branched alkylene or alkenylene, or such alkylene and alkenylene groups substituted with halo, hydroxy, keto, carboxy, alkoxycarbonyl, amino, or alkylamino groups. The structures

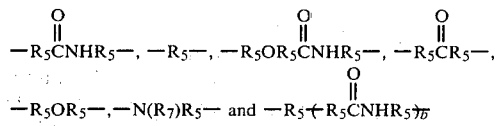

and most desirable, with

being preferred.

$R_5$ and $R_7$ may represent the same or different alkylene or alkenylene groups. These groups should generally contain up to about 10 carbon atoms, and may be noncyclic or cyclic such as cyclohexylene or phenylene. Fully saturated, straight or branched chain hydrocarbons of from 1 to about 5 carbon atoms are preferred. They ordinarily will contain no more than two halo, hydroxy, keto, carboxy, alkoxycarbonyl, amino or alkylamino substituents. The keto, hydroxy, carboxy or amino substituents are preferred. Halogen substituents include bromine, chlorine or nonradioactive iodine, and the alkoxy, alkylamino or alkoxycarbonyl substituents should generally contain normal or branched hydrocarbons of from 1 to about 3 carbon atoms.

Representative $R_5$ groups may be ethylene, methylene, 2-hydroxy propylene, 3-hydroxypropylene, 3-ethyl-2-pentynylene, isopropylene, butylene, isobutylene, 3-aminoisobutylene, 3-dimethylaminoisobutylene, 2-hydroxyisobutylene, heptylene, 2-aminoheptylene, hexylene, 2-ethylheptylene, 2-hydroxyheptylene, 1-carboxyethylene, 3-carboxymethyl hexylene, 3-methoxyheptylene and 1-hydroxymethylethylene. It is most preferred that $R_5$ be an unsubstituted alkylene of 3 to 5 carbon atoms, for example butylene, although substituents such as hydroxyl may be added to improve the water solubility of the tracer. Suitable $R_7$ groups include all of the foregoing except that the radicals will be monovalent.

Some exemplary ring-containing radicals Z are disclosed below:

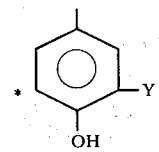

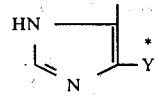

-continued

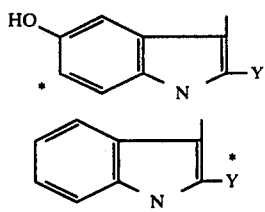

wherein Y is hydrogen, halo or lower alkyl up to about 7 carbon atoms. These radicals may then be radiolabeled, preferably radioiodinated with one radioiodine atom at the probable positions of labeling indicated with an asterisk. Also, the radicals may be radioiodinated at the Y position where Y was hydrogen prior to radioiodination. The radioiodine is generally $^{125}I$ but other iodine isotopes such as $^{131}I$ may also be used. Radioiodination is preferably carried out after coupling of the ring-containing radical to the barbiturate is complete, but radioiodination of the radical also may be accomplished prior to coupling.

The aliphatic radioiodinated or radioiodinatable radicals which are within the scope of this invention are ordinarily straight chain, substituted or unsubstituted hydrocarbons of up to about 10 carbon atoms. These hydrocarbons may be substituted with the same groups as $R_5$ or $R_7$ as set forth supra, but there must be at least one hydroxyl group or double bond in the radical if it is to be radioiodinatable. $^{125}I$ vinyliodides of $C_3$ to $C_7$ hydrocarbons are to be preferred. It is within the scope of this invention to radioiodinate both a radioiodinatable ring as well as the aliphatic linking group joining the ring to the barbiturate moiety. The product tracers are preferably alkenyl groups containing one double bond, about from 3 to 7 carbon atoms and radioiodine substituted at the double bond or $\alpha$ thereto.

The following table includes certain representative tracers within the scope of this invention. Suitable tracer precursor compounds would be identical to those in this table except that hydrogen is to be substituted for $^{125}I$ or $^{131}I$. Compound no. 1 is the preferred tracer.

TABLE-continued
Radioiodinated Ring-Containing Barbiturate Derivatives

| Compound No. | barbiturate | linking group | radioiodinated ring |
|---|---|---|---|
| 6. | 5-allyl-5-(1-methylbutyl) N-methyl barbiturate with $CH_2=CHCH_2$ and $CH_3(CH_2)_2CH(CH_3)$ substituents | $-(CH_2)_6CH\begin{matrix}CH_2CNH-CH_2-\\CH_2CNH-CH_2-\end{matrix}$ (with C=O groups) | 3-($^{125}I$)-4-hydroxyphenyl (two rings shown) |
| 7. | 2-thio-5-(2-methylthioethyl)-5-(1-methylbutyl) N-methyl barbiturate | $-(CH_2)_2\overset{O}{C}-NH-\overset{CH_2}{CH}-\overset{O}{C}-NH-\overset{CH_2}{CH}-COOH$ | two 3-($^{125}I$)-4-hydroxy-5-methylphenyl rings |
| 8. | 1,3-dimethyl-5-methyl-5-(cyclohexenyl) barbiturate | $-(CH_2)_4-\overset{S}{C}-NH-\overset{C-OCH_3}{CH}-CH_2-$ | 4-($^{125}I$)-imidazolyl |
| 9. | 5-ethyl-5-phenyl N-methyl barbiturate | $-(CH_2)_4\overset{O}{C}-(CH_2)_4\overset{O}{C}-NH-\overset{COOH}{CH}-CH_2-$ | 3,5-di($^{125}I$)-4-hydroxyindolyl |
| 10. | 5-ethyl-5-phenyl N-methyl barbiturate | $-(CH_2)_6-\overset{O}{\underset{OCH_3}{P}}-O-CH_2-$ | 4-($^{125}I$)-imidazolyl |
| 11. | 5-ethyl-5-phenyl N-methyl barbiturate | $-(CH_2)_6-\overset{O}{\underset{O}{P}}-O-(CH_2)_3-$ | 4-($^{125}I$)-imidazolyl |
| 12. | 5-(2-bromoallyl)-5-isopropyl barbiturate | $-CH_2-\overset{CH_3}{\underset{CH_2}{CH}}-\overset{O}{C}-N\overset{CH_3}{\underset{CH}{H}}-\overset{CH_3}{\underset{CH_3}{CH}}-$ | 3-($^{125}I$)-4-hydroxy-5-methylphenyl |
| 13. | 5-ethyl-5-phenyl barbiturate | $-CH_2-\overset{O}{C}-CH_2-\overset{O}{C}-NH-(CH_2)_2-$ | 3-($^{125}I$)-4-hydroxyphenyl |
| 14. | 5-ethyl-5-phenyl N-methyl barbiturate | $-CH_2-\overset{O}{C}-NH-CH_2-CH_2-$ | 3-($^{125}I$)-4-hydroxy-5-methylphenyl |

TABLE-continued
Radioiodinated Ring-Containing Barbiturate Derivatives

| Compound No. | barbiturate | linking group | radioiodinated ring |
|---|---|---|---|
| 15. | 5-ethyl-5-phenyl barbiturate (N-H, N-substituted) | $-CH_2-\overset{O}{\underset{\|}{C}}-NH-$ | $^{125}I$-substituted hydroxyphenyl |
| 16. | 5-ethyl-5-phenyl barbiturate (N-H, N-substituted) | $-CH_2\overset{OH}{\underset{\|}{C}}H\ CH_2\overset{O}{\underset{\|}{C}}-CH_2-\overset{O}{\underset{\|}{C}}-NH-\overset{H}{\underset{\|}{C}}H-$ | $^{125}I$-imidazole |
| 17. | 5-ethyl-5-phenyl barbiturate (N-H, N-substituted) | phenyl-$\overset{O}{\underset{\|}{C}}-NH-\overset{HOCH_2\ \ CH_2OH}{\underset{\|}{C}H}-$ | $^{125}I$-imidazole |
| 18. | 5-ethyl-5-phenyl barbiturate (N-, N-substituted) | $-CH_2-\overset{O}{\underset{\|}{C}}-NH-CH_2-$ <br><br> $-CH_2-\overset{O}{\underset{\|}{C}}-NH-$ | $^{125}I$-imidazole <br><br> $^{125}I$-hydroxyphenyl |
| 19. | 5-ethyl-5-phenyl barbiturate (N-, N-substituted) | $-CH_2-\overset{O}{\underset{\|}{C}}-NH-\overset{\overset{O}{\underset{\|}{C}}-OH}{\underset{\|}{C}H}-CH_2-$ <br><br> $-CH_2-\overset{O}{\underset{\|}{C}}-NH-CH_2\overset{OH}{\underset{\|}{C}}H\ CH_2-$ | $^{125}I$-hydroxyphenyl <br><br> $^{125}I$-imidazole |
| 20. | 5-ethyl-5-phenyl barbiturate (N-H, N-substituted) | $-(CH_2)_2-\overset{O}{\underset{\|}{C}}-O-CH_2-$ | $^{125}I$-imidazole |
| 21. | 5-ethyl-5-phenyl barbiturate (N-H, N-substituted) | $-\overset{OH}{\underset{\|}{C}H}-CH_2-\overset{O}{\underset{\|}{C}}-CH_2\overset{O}{\underset{\|}{C}}-O-CH_2-$ | $^{125}I$-imidazole |
| 22. | 5-ethyl-5-phenyl barbiturate (N-H, N-substituted) | $-CH_2-CH(Br)(CH_2)_2-$ | $^{125}I$-hydroxyphenyl |

TABLE-continued

Radioiodinated Ring-Containing Barbiturate Derivatives

| Compound No. | barbiturate | linking group | radioiodinated ring |
|---|---|---|---|
| 23. | (structure with barbiturate, phenyl, CH₃CH₂) | —(CH₂)₂—CH— with CH₂Br substituent | phenyl with $^{125}I$ and OH |
| 24. | (structure with barbiturate, phenyl, CH₃CH₂) | — | phenyl with CH₃ and $^{125}I$ |
| 25. | (structure with barbiturate, phenyl, CH₃CH₂) | —(CH₂)₂— | phenyl with $^{125}I$ and OH |

The tracers of this invention may be prepared by numerous techniques known to those in the art or by the following novel process. This process involves first providing an alkali metal salt of the barbiturate to which the assay is directed, usually the potassium or sodium salt. If it is desired to conduct the subsequent reactions in organic solvents a quaternary ammonium salt may be synthesized as disclosed in U.S. Pat. No. 4,036,823. Then the salt is reacted with an ω-halogenated group designated

XR₅COB, wherein R₅ is defined above, X is halogen such as bromine and B is lower alkyl from 1 to about 7 carbon atoms, preferably methyl or ethyl. The method of Cook et al., *Quantitative Analytic Studies in Epilepsy*, pp. 39–57 (1976), using methyl 5-bromo-valerate is preferred although the procedure disclosed in U.S. Pat. No. 3,817,837 is satisfactory. The reaction with ⅜-halogenated

XR₅COB produces barbiturate-3-(ω-carboxylic acid ester), barbiturate-1-(ω-carboxyic acid ester) and barbiturate-1,3-(ω-carboxylic acid ester). The mono substituted compound is the preferred species. It may be separated from the disubstituted barbiturate by thin layer chromatography on silica gel and extraction into ethanol, or by chromatography on an ion exchange resin. Other separatory techniques will be apparent to the ordinary skilled artisan. The monocarboxylic acid may be produced by hydrolysis of the ester in accordance with either Cook et al. or U.S. Pat. No. 3,817,837.

The monosubstituted barbituric acid is then coupled to an amino-containing, radioiodinatable or radioiodinated radical, e.g., a radioiodinatable ring-containing compound, a radioiodinatable aliphatic compound such as butyldiene or a pre-radioiodinated compound containing either a ring or aliphatic group. The advantage to employing a preradioiodinated, amino substituted ring-containing compound such as radioiodinated tyrosine or histamine is that any radioiodination degradation products may be removed from the preradioiodinated compound before it is conjugated with the barbiturate moiety, thereby resulting in less waste of barbiturate. Alternatively, the tracer may be purified after it has been radioiodinated. In one alternative for coupling the amino-substituted radical and the barbiturate carboxylic acid, a lower alkyl chloroformate or pivaloyl chloride are reacted with the monocarboxylic acid to generate mixed anhydrides. This reaction is carried out in any conventional aprotic solvent at low temperature (0°–10° C.) under anhydrous conditions, although dioxane is the preferred solvent. One equivalent of organic base such as triethylamine is added to consume hydrochloric acid generated in the mixed anhydride formation. The ring-containing amino compound and the mixed anhydride are then combined in either aqueous solution or a mixed organic solvent; the reaction of the amino compound with the anhydride is apparently more rapid than hydrolysis of the anhydride.

Another convenient reaction for coupling the barbituric acid and amino-substituted radioiodinatable or radioiodinated compound is a carbodiimide condensation performed substantially according to U.S. Pat. No. 3,766,162. This patent discloses forming a peptide bond between a barbituric acid derivative and a protein or polypeptide which can confer antigenicity to the barbituric acid derivative. However, proteins or peptides of a size sufficient to confer antigenicity could adversely affect the binding of tracer to antibody in relation to the barbiturate to be assayed. Also, such proteins and peptides are unstable to long-term storage when radioiodinated. Thus it is necessary when forming the above-defined linking group

by the process of U.S. Pat. No. 3,766,162 that one employ a nonantigenic polypeptide. Such a polypeptide would ordinarily have a molecular weight of less than about 2000 and contain no more than about ten radioiodinatable rings, i.e., a would be no more than about 10.

Isolation of the conjugate is accomplished by addition of the reaction mixture to acidified water. The precipitate obtained can be recrystallized from ethanol. Further purification may be accomplished by preparative thin layer chromatography, gel filtration, affinity chromatography, or other suitable procedures.

The tracers or the preradioiodinated amino-substituted compounds may be prepared by any one of the following methods:
(1) Chloramine T Method of Hunter-Greenwood, W. Hunter, R. C. Greenwood, Nature, 194, 495 (1962);
(2) Iodine Monochloride Method, M. Ceska, F. Grossmuller, U. Lindkvist, Acta Endocrinologia, 64, 111–125 (1970);
(3) Isotopic Exchange Method, R. E. Counsell, V. V. Ranade, P. Pocha, R. E. Willette, W. Diguilio, J. Pharmaceut. Sciences, 57, 1657 (1968);
(4) Electrolytic Iodination, R. Pennisi, U. Rosa, J. Nuclear Biol. and Medicine, 13, 64 (1964); and
(5) Enzymatic Iodination, H. Van Vanakis, J. J. Langone, L. J. Riceberg, L. Levine, Cancer Research 34, 2546–2552 (1974).

The marginally water soluble products of this invention may be iodinated in inert solvents such as water or water-alcohol mixtures.

Separation of unreacted radioactive iodine is accomplished by gel filtration and the use of aqueous solvents that elute selectively unreacted inorganic iodide and the desired iodinated product.

An additional method for making the tracers of this invention is to convert an aminoaryl-substituted barbiturate to a diazonium salt, followed by reaction with an inorganic radioiodide such as $^{125}I$ NaI to replace the diazonium group with $^{125}I$. A representative tracer which could be produced by such a method is designated no. 24 in the table supra.

While the preferred tracers of this invention will contain the above radioiodinated rings it is also within the scope of this invention to substitute radioiodinated aliphatic radicals at the nitrogen atoms of the barbiturate ring. This can be readily accomplished by synthesizing a 1 or 3, or 1 and 3 alkanol-substituted barbiturate, followed by reaction of the alcohol with $^{125}I$ $PI_3$ or HI in the presence of an appropriate catalyst. A representative compound produced by such a process is $^{125}I$ 5-ethyl-5'-phenyl-3-(2-iodoethyl)-barbituric acid.

Alternatively the same positions of the barbiturate could be substituted with a polyalkene, e.g., an alkydiene such as 2,4-pentadiene. The pair of double bonds in the resulting barbiturate derivative could then be reacted to add iodine at or immediately adjacent to one double bond, yielding for example 5-ethyl-5'-phenyl-3-(1-iodo-2,4-pentadienyl)-barbituric acid. This method should not be used in preparing propallylonal, hexobarbital or secobarbital tracers.

The invention will be more fully understood by reference to the following examples.

EXAMPLE 1

A. A mixture of 1.17 m mole of 3-sodium phenobarbital and 0.25 gm of methyl 5-bromovalerate in 7 ml of dimethylformamide is heated with stirring to 60° C. for 3 hours. The reaction mixture was added to 7 ml of ⅓ saturated aqueous ammonium sulfate and allowed to crystallize for 24 hours to yield crude phenobarbital-3-(5-valeric acid methyl ester). On recrystallization from 10 ml of hot methanol 22 mg of crystalline material is obtained, m.p. 270°–280° C.

B. The ester obtained in 1-A was hydrolyzed by dissolving the ester in 0.5 M HCl in 50% aqueous tetrahydrofuran at room temperature for 24 hours. The solvent was evaporated, redissolved in water and extracted into ethyl acetate. The solid residue was used in the next step.

C. 100 mg of phenobarbital 3-(5-valeric acid) was added to 2.0 ml of dioxane containing a trace of triethylamine. 50 μl of 10% ethyl chloroformate in dioxane were then added to the solution and stirred for 30 minutes at about 10° C. until the mixed anhydride was formed.

100 mg of histamine as the free base was dissolved in 1 ml of distilled water and cooled to about 10° C. The aqueous histamine was rapidly mixed with the cold mixed anhydride solution and vigorously for 30 minutes at about 10° C., followed by two more hours of reaction while the temperature of the solution was allowed to slowly come to room temperature. When the reaction was completed the reaction mixture was removed and the residual product oil was placed under a vacuum for 12 hours.

Analogous products of the present invention can be made by substituting other ω-halocarboxylic acid alkyl or alkenyl esters for methyl 5-bromovalerate, or by substituting in place of histamine other ring-containing amino compounds such as tyrosine, tyrosinol, 4-(2-aminoethyl) phenol, histidine, histidinol, or amino-terminated polypeptides containing one or more of the radioiodinatable rings as defined above. Alternatively, the positions of the amino and carboxyl groups may be interchanged so that the barbiturate N-substituent terminates in an amino group while a carboxyl-substituted ring-containing compound is supplied.

EXAMPLE 2

Radioiodination of phenobarbital-3-(5-valeryl-N-histamine) was effected by the method of Hunter and Greenwood. 4.5 μg of the product of Example 1 was added to a clean 10 ml bottle with 0.1 ml of 0.5 molar phosphate buffer, pH 8.0. To this mixture was added 1 mCi of sodium iodide $^{125}I$ in 10 μl of 0.1 N NaOH, followed by 10 μl of an aqueous solution of chloramine T (50 mg in 10 of distilled water).

After reaction at room temperature for 90 seconds with occasional shaking the reaction was quenched by the addition of 10 μl of a solution of sodium metabisulfite (300 mg in 10 ml of distilled water). The reaction mixture then contained both monosubstituted and disubstituted phenobarbital tracers which may be separated and purified by chromatography on an anion exchange column or by other purification methods well known to the skilled artisan.

EXAMPLE 3

The mixed monosubstituted and disubstituted tracer of Example 2 is used as the labeled antigen in a competitive radioimmunoassay of phenobarbital wherein an antibody coated tube is employed to separate the bound and unbound phases.

100 μl of patient serum diluted 1:101 in distilled water is added to a rabbit anti-phenobarbital serum coated tube which may be prepared in known fashion, e.g., Catt et al., "Science" 158:1570 (1967). Standards and controls are prepared in the conventional manner. Then to each tube is added 1.0 ml of a tracer-buffer reagent containing about 1 nCi of tracer in a solution of 0.15 M sodium chloride, 0.01 M phosphate buffer, 0.0008 M sodium EDTA and 0.02 M sodium azide. The contents of the tubes are mixed carefully and incubated for 45 minutes at 37°±2° C. The contents of each tube are aspirated or decanted into appropriate containers and counted in a gamma counter with the window suitably adjusted for iodine-125.

The above examples and other specific information contained herein are for purposes of illustration only. Such alterations and modifications thereof as would be apparent to those skilled in the art are deemed to fall within the scope and spirit of the invention bearing in mind that the invention is defined only by the appended claims.

We claim:

1. In a radioimmunoassay for a predetermined 5,5'-substituted barbiturate wherein a barbiturate tracer is used, the improvement comprising using as said tracer said 5,5'-barbiturate having a radioiodinated substituent at the 1, 3 or 1 and 3 positions of the barbiturate ring, with the proviso that said substituent be nonantigenic and have a molecular weight of less than about 2000.

2. The improvement of claim 1 in which the radioiodinated substituent is selected from the group consisting of $L(Z)_n$ and radioiodine-substituted alkyls and alkenyls, wherein L is a linking group, Z is a radioiodinated ring and n ranges from 1 to about 10.

3. The improvement of claim 2 in which the radioiodinated substituent is $L(Z)_n$.

4. The improvement of claim 2 in which the radioiodinated substituent is a radioiodine-substituted alkenyl.

5. The improvement of claim 4 in which the alkenyl contains one double bond, about from 3 to 7 carbon atoms and the radioiodine is substituted at the double bond or α thereto.

6. The improvement of claim 3 in which L is —$R_5$—

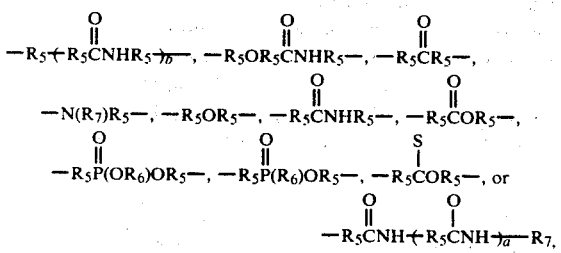

and wherein
$R_5$ is selected from the group comprising a bond and an unsubstituted or substituted hydrocarbon;
a ranges from 1 to about 10;
b is 2 or 3;
$R_6$ is alkyl of from 1 to about 6 carbon atoms; and
$R_7$ is hydrogen or an unsubstituted or substituted hydrocarbon.

7. The improvement of claim 6 in which L is

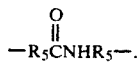

8. In a radioimmunoassay for a 5,5'-substituted barbiturate wherein a barbiturate tracer is used, the improvement comprising using as said tracer a compound of the formula

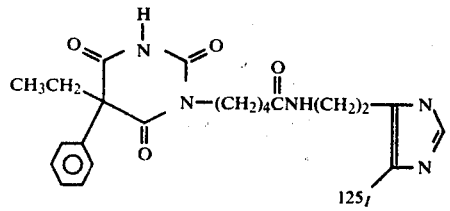

9. A tracer for use in the assay of a barbiturate comprising said barbiturate having a radioiodinated substituent at the 1, 3 or 1 and 3 positions of the barbiturate ring, with the proviso that said substituent be nonantigenic and have a molecular weight of less than about 2000.

10. The tracer of claim 9 wherein the substituent is a polypeptide having from 2 to about 10 amino acid resides.

11. The tracer of claim 10 having two amino acid residues.

12. A compound useful in the radioimmunoassay of barbiturates, said compound selected from the group consisting of compounds having the formula:

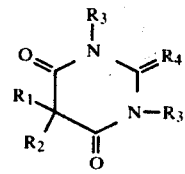

wherein
(a) $R_1$, $R_2$, and $R_4$ are identical to the substituents found at these positions in the barbiturate which is to be assayed;
(b) at least one $R_3$ is a straight or branched chain alkylpolyene; and
(c) if only one $R_3$ is said alkylpolyene then the remaining $R_3$ is identical to the substituent at this position in the barbiturate which is to be assayed.

13. A compound useful in the radioimmunoassay of barbiturates, said compound selected from the group consisting of compounds having the formula:

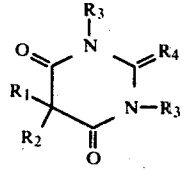

wherein
(a) $R_1$, $R_2$ and $R_4$ are identical to the substituents found at these positions in the barbiturate which is to be assayed;
(b) at least one $R_3$ is the group $L(Z)_n$ in which L is a linking group, n ranges from 1 to about 10 and Z is a radioiodinatable ring selected from the group of imidazole, pyrrole, furan or thiophene rings; and
(c) if only one $R_3$ is said group $L(Z)_n$ then the remaining $R_3$ is identical to the substituent at this position in the barbiturate which is to be assayed.

14. A compound useful in the radioimmunoassay of barbiturates and having the formula:

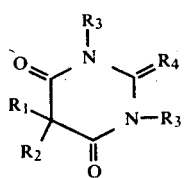

wherein
(a) $R_1$, $R_2$ and $R_4$ are identical to the substituents found at these positions in the barbiturate which is to be assayed;
(b) at least one $R_3$ is the group $L(Z)_n$ in which L is a linking group, n ranges from 1 to about 10 and Z is imidazole; and
(c) if only one $R_3$ is said group $L(Z)_n$ then the remaining $R_3$ is identical to the substituent at this position in the barbiturate which is to be assayed.

15. A tracer compound for use in barbiturate radioimmunoassay having the formula:

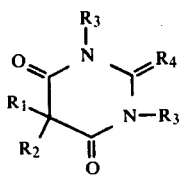

wherein:
(a) $R_1$ and $R_2$ are hydrogen, monohalo hydrocarbon, ether, thioether, or alkyl, alkenyl, cycloalkyl, cycloakenyl or aryl hydrocarbon of from 1 to about 8 carbon atoms;
(b) $R_4$ is O or S;
(c) at least one $R_3$ is a radioiodinated radical, with the proviso that said radical be nonantigenic and have a molecular weight of less than about 2000; and
(d) if only one $R_3$ is a radioiodinated radical then the remaining $R_3$ is hydrogen or hydrocarbon of from 1 to about 4 carbon atoms.

16. A barbiturate derivative of the formula:

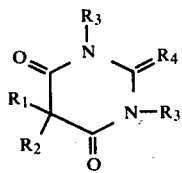

wherein:
(a) $R_1$ and $R_2$ are hydrogen, monohalo hydrocarbon, ether, thioether, or alkyl, alkenyl, cycloalkyl, cycloalkenyl or aryl hydrocarbon or from 1 to about 8 carbon atoms;
(b) $R_4$ is O or S;
(c) at least one $R_3$ is the group $L(Z)_n$ in which L is a linking group, Z is a radioiodinated ring and n ranges from 1 to about 10, with the proviso that said group be nonantigenic and have a molecular weight of less than about 2000; and (d) if only one $R_3$ is $L(Z)_n$ then the remaining $R_3$ is hydrogen or hydrocarbon of 1 to about 4 carbon atoms.

17. The derivative of claim 16 wherein L is

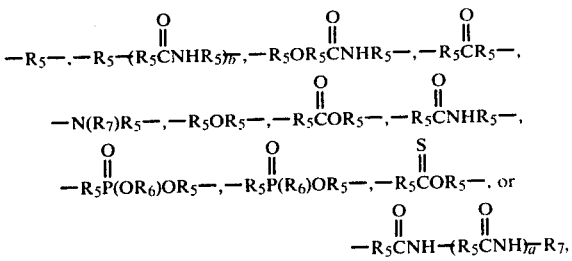

with $R_5$ being selected from the group comprising a bond and an unsubstituted or halo, hydroxy, keto, carboxy, alkoxy carbonyl, amino or aminoalkyl substituted cyclic, normal or branched alkyl or alkenyl radical;
a ranges from 1 to about 10;
b is 2 or 3;
$R_6$ is alkyl of from 1 to about 6 carbon atoms; and
$R_7$ is hydrogen; or an unsubstituted or halo, hydroxy, keto, carboxy, alkoxy carbonyl, amino or aminoalkyl substituted cyclic, normal or branched alkyl or alkenyl radical.

18. The derivative of claim 16 wherein Z is a radioiodinated phenol, imidazole,, indole, pyrrole, furan or thiophene radical.

19. The derivative of claim 16 wherein L is

and $R_5$ is selected from the group comprising a bond and an unsubstituted or halo, hydroxy, keto, carboxy, alkoxy carbonyl, alkylamino or amino substituted cyclic, normal or branched alkyl or alkenyl radical.

20. The derivative of claim 17 wherein $R_5$ is a hydroxy, amino or carboxy substituted alkyl radical.

21. The derivative of claim 17 wherein L is

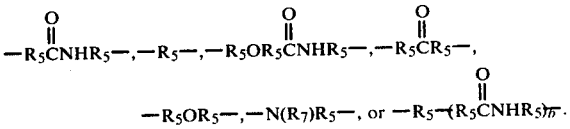

22. A compound having the formula:

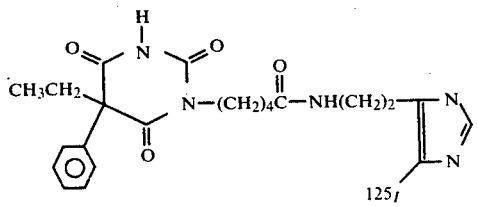

23. A compound having the formula:

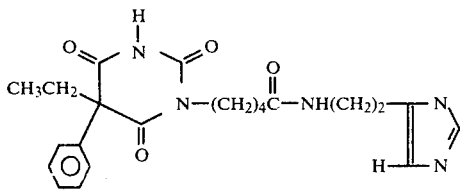

24. A compound selected from the group consisting of compounds having the formula:

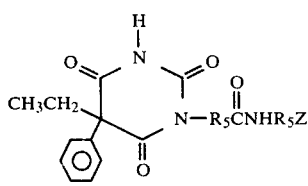

wherein
(a) $R_5$ is alkyl or alkyl substituted with one or two hydroxy or amino groups; and
(b) Z is a phenol or imidazole radical.

25. The compound of claim 24 wherein the phenol or imidazole radicals are radioiodinated.

26. The method of making a novel barbiturate which comprises
(a) reacting a barbiturate alkali metal salt with an ω-halogenated normal or branched chain alkyl acid ester having the structure

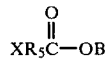

wherein $R_5$ may contain, in addition to carbon and hydrogen, keto, alkoxy, alkoxycarbonyl, hydroxyl, alkylamino or amino groups; X is halogen; and B is lower alkyl from 1 to 7 carbon atoms;
(b) hydrolyzing the reaction product to form a free carboxylic acid,
(c) reacting said free acid with a member of the group consisting of alkyl chloroformate and pivaloyl chloride in the presence of an organic base to form a mixed anhydride, and
(d) reacting said mixed anhydride with a radioiodinated or radioiodinatable amino compound.

27. The method of claim 26 in which the radioiodinatable compound is tyrosine, tyrosinol, 4-(2-aminoethyl)-phenol, histidine, histidinol, histamine or an amino-terminated, nonantigenic polypeptide containing one or more radioiodinatable rings.

28. The method of claim 26 including the additional step of radioiodinating the compound.

29. In a method for making a radiolabeled tracer for barbiturate immunoassay wherein a barbiturate derivative carrying a radioiodinatable group is radioiodinated, the improvement comprising substituting the radioiodinatable group onto at least one nitrogen atom of the barbiturate pyrimidine ring, with the proviso that said radioiodinatable group be nonantigenic and have a molecular weight of less than about 2000.

30. A tracer for use in the assay of a barbiturate, comprising a compound of the formula

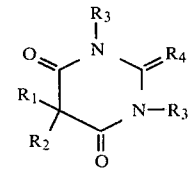

wherein
(a) $R_1$, $R_2$ and $R_4$ are identical to the substituents found at these positions in the barbiturate which is to be assayed;
(b) at least one $R_3$ is the group $L(Z)_n$ in which L is a linking group, n is 1, Z is a phenol, indole or imidazole radical, with the proviso that $L(Z)_n$ be nonantigenic and have molecular weight of less than about 2000; and
(c) if only one $R_3$ is said group $L(Z)_n$ then the remaining $R_3$ is identical to the substituent at this position in the barbiturate which is to be assayed.

31. A tracer for use in the assay of a barbiturate selected from the group of propallylonal, phenobarbital, hexobarbital, secobarbital, methitural, amobarbital, pentobarbital, butabarbital and thiopental, comprising said barbiturate having a radioiodinated substituent at the barbiturate 1 position.

* * * * *